US012770380B2

(12) United States Patent
Cota et al.

(10) Patent No.: US 12,770,380 B2
(45) Date of Patent: Oct. 20, 2026

(54) METHOD FOR ANALYSIS OF ORAL X-RAY PICTURES AND RELATED ANALYSIS SYSTEM

(71) Applicant: CEFLA S.C., Imola (IT)

(72) Inventors: Giuseppe Cota, Rovigo (IT); Gaetano Scaramozzino, Rovigo (IT); Alessandro Berto, Rovigo (IT)

( * ) Notice: Subject to any disclaimer, the term of this patent is extended or adjusted under 35 U.S.C. 154(b) by 244 days.

(21) Appl. No.: 18/833,907

(22) PCT Filed: Dec. 13, 2022

(86) PCT No.: PCT/IT2022/050324

§ 371 (c)(1),
(2) Date: Jul. 28, 2024

(87) PCT Pub. No.: WO2023/148793

PCT Pub. Date: Aug. 10, 2023

(65) Prior Publication Data

US 2025/0131697 A1 Apr. 24, 2025

(30) Foreign Application Priority Data

Feb. 2, 2022 (IT) ........................ 102022000001826

(51) Int. Cl.
*G06K 9/00* (2022.01)
*G06T 7/00* (2017.01)
(Continued)

(52) U.S. Cl.
CPC .......... *G06V 10/778* (2022.01); *G06T 7/0012* (2013.01); *G06T 7/13* (2017.01);
(Continued)

(58) Field of Classification Search
CPC ...... G06V 10/778; G06V 10/25; G06V 10/26; G06V 10/32; G06V 10/764;
(Continued)

(56) References Cited

U.S. PATENT DOCUMENTS 8,761,493 B2 * 6/2014 Chen .......................... G06T 3/06 348/42
9,972,083 B2 * 5/2018 Souza ................... G06T 7/0012
(Continued)

FOREIGN PATENT DOCUMENTS

WO 2019002631 1/2019

OTHER PUBLICATIONS

Szymon Plotka et al., Convolutional Neural Networks in Orthodontics: a review,arxiv.org, Cornell University Library, 201 Olin Library, Cornell University, Itaca, NY 14853, Apr. 18, 2021 The whole document.

*Primary Examiner* — Shervin K Nakhjavan
(74) *Attorney, Agent, or Firm* — Themis Law

(57) ABSTRACT

A computer-implemented method of analyzing X-Ray pictures, particularly oral X-Ray pictures, includes an operational inference phase, with the following steps: detecting an X-Ray image; and performing at least one inference module to obtain the detection and distinction of teeth and anatomical parts of the mouth, as well as pathological and non-pathological conditions. A system for analyzing X-Rays is also disclosed.

17 Claims, 11 Drawing Sheets

(51) Int. Cl.

| | |
|---|---|
| ***G06T 7/13*** | (2017.01) |
| ***G06V 10/25*** | (2022.01) |
| ***G06V 10/26*** | (2022.01) |
| ***G06V 10/32*** | (2022.01) |
| ***G06V 10/764*** | (2022.01) |
| ***G06V 10/77*** | (2022.01) |
| ***G06V 10/778*** | (2022.01) |
| ***G06V 20/70*** | (2022.01) |
| ***G16H 30/40*** | (2018.01) |
| ***G16H 50/20*** | (2018.01) |
| *A61B 6/51* | (2024.01) |
| *G06V 10/44* | (2022.01) |

(52) U.S. Cl.

CPC .............. *G06V 10/25* (2022.01); *G06V 10/26* (2022.01); *G06V 10/32* (2022.01); *G06V 10/764* (2022.01); *G06V 10/7715* (2022.01); *G06V 20/70* (2022.01); *G16H 30/40* (2018.01); *G16H 50/20* (2018.01); *A61B 6/51* (2024.01); *G06T 2207/10116* (2013.01); *G06T 2207/20081* (2013.01); *G06T 2207/20084* (2013.01); *G06T 2207/30036* (2013.01); *G06V 10/44* (2022.01); *G06V 2201/033* (2022.01)

(58) Field of Classification Search

CPC .... G06V 10/7715; G06V 20/70; G06V 10/44; G06V 2201/033; G06T 7/0012; G06T 7/13; G06T 2207/10116; G06T 2207/20081; G06T 2207/20084; G06T 2207/30036; G06T 7/12; G16H 30/40; G16H 50/20; A61B 6/51

See application file for complete search history.

(56) References Cited

U.S. PATENT DOCUMENTS

| | | | | |
|---|---|---|---|---|
| 10,460,839 | B1 | 10/2019 | Ricci | |
| 10,997,727 | B2 * | 5/2021 | Xue ...................... | G06T 7/0012 |
| 11,648,094 | B2 * | 5/2023 | Reynard .............. | A61C 9/0046 433/215 |
| 12,131,462 | B2 * | 10/2024 | Amiri Kamalabad .. | G06T 7/174 |
| 12,154,243 | B2 * | 11/2024 | Cofar ...................... | G06T 17/00 |
| 12,555,283 | B2 * | 2/2026 | Ezhov .................. | A61B 5/1075 |
| 2020/0175678 | A1 * | 6/2020 | Abraham ............... | G16H 30/40 |
| 2022/0012888 | A1 * | 1/2022 | Chen ........................ | A61B 6/51 |
| 2023/0218370 | A1 * | 7/2023 | Azernikov ............. | A61C 9/004 345/423 |
| 2025/0318904 | A1 * | 10/2025 | Matov .................... | A61C 7/002 |

* cited by examiner

METHOD FOR ANALYSIS OF ORAL X-RAY PICTURES AND RELATED ANALYSIS SYSTEM

The present invention relates to a method for analysing oral X-Ray pictures and its analysis system.

FIELD OF INVENTION

The present invention relates to a computer-implemented method for analysing X-Ray pictures, particularly oral X-Ray pictures to detect items of interest, which in the case of oral X-Ray pictures, typically involve information for dentists (teeth, pathology, etc.).

In more detail, the invention concerns a computer-implemented method and system that, by means of techniques based on so-called computer vision and artificial neural networks enables, among other things, accurate analysis of X-Rays in order to detect the position and shape of the main anatomical parts of the body zone being analysed, the position and shape of pathological findings, such as cavities and apical lesions, and non-pathological findings, such as fillings.

In the following, the description will be concerned with oral X-Ray pictures, but it is very clear that it should not be considered limited to this specific use. The parts that will mainly be examined are those of the mouth (teeth, lower alveolar nerves, sinuses and condyles) and items related to pathological, non-pathological conditions and dental therapies (e.g., fillings and root canal treatments).

Note on Technique

As is well known currently in the dental field, the analysis of X-Ray images for the recognition of anatomical parts and to detect any pathological phenomena is, in most cases, carried out entirely by the dentist without any computerized support other than that of simple image visualization.

However, the analysis of anatomical zones performed on an X-Ray is influenced by the dentist's level of experience and expertise, as well as his or her level of concentration and fatigue at the time he or she performs the analysis.

In addition, inexperience about a particular disease and inattention could lead to incomplete or incorrect diagnoses or the wrong therapies being prescribed.

To address this issue, artificial intelligence-based systems have been emerging in recent years for the processing and analysis of dental X-Ray pictures (Chen, Stanley, & Att., 2020). Several artificial intelligence systems are known to automatically recognize pathologies, abnormalities, and other conditions (implants, crowns, root canal treatments, etc.) from X-Ray images. Such known systems are based on computer vision and machine learning methods. In particular, the main components of machine learning programs of the major known systems are based on neural networks, which enable the localization of regions of interest and their classification.

A common disadvantage of systems according to the known technique is that they do not define the shapes of the findings made, but define, around an element of interest, only its bounding box, that is, a square shaped container that contains it. This drawback places limitations on the detection of some conditions, such as the detection of tooth roots invading a maxillary sinus or a mandibular canal that houses one of the two inferior alveolar nerves. In particular, the latter condition is of special interest because extraction of the third molar (wisdom tooth) is commonly practiced and, if an accurate X-Ray evaluation is not performed, there is a risk of causing temporary or permanent neurological damage to the inferior alveolar nerve and, in the worst case, causing partial paresis of the lower lip.

It seems clear that solutions according to the known technique are potentially costly because they can also create temporary or permanent damage to the patient.

Patent application WO 2019/002631 A and U.S. Pat. No. 10,460,839 B1 are part of the known technique.

PURPOSE OF THE INVENTION

In view of the above, it is, therefore, the purpose of the present invention to propose a system and method of analysing X-Ray pictures and in particular oral X-Ray pictures which exceeds the limitations of the known technique.

Another purpose of the present invention is for a support system for physician-radiologists, and dentists in particular, that enables the localization and detection of the shape of anatomical parts, pathologies, and other conditions from X-Ray images.

An additional purpose of the present invention is to reduce as much as possible the risk of inaccurate or erroneous diagnoses, therapies, and treatments by the treating dentist.

OBJECT OF THE INVENTION

Therefore, it is a specific object of the present invention to provide a Computer-implemented method for analysing X-Ray pictures, particularly oral X-Ray pictures, comprising an operational inference phase, comprising in turn the following phases: Detecting an X-Ray image; and performing at least one inference module to obtain the detection and distinction of said teeth and the detection and distinction of anatomical parts of the mouth and/or the detection and distinction of pathological and non-pathological findings.

Also, according to the invention, said phase of performing at least one inference module may include the following subphases: Performing an anatomical model inference module; performing a tooth model inference module; performing an inference module for the model of findings in the mouth; and performing an inference module for the model of findings for a single tooth.

Still according to the invention, said inference module for the model of single tooth findings can be performed following said teeth model inference module, and said anatomical model inference module, said teeth model inference module and said mouth findings model inference module (22*c*) can be performed in parallel.

Advantageously according to the invention, said anatomical model inference module and said single tooth findings model inference module can acquire as input the geometric coordinates that make up the tooth outlines detected by said tooth model inference module.

Further according to the invention, each said anatomical model inference module, tooth model inference module, mouth findings model inference module and single tooth findings model inference module include a pre-processing phase, comprising in turn the subphases of: Contrast limited adaptive histogram equalization (CLAHE), so as to change the image in contrast; and image resizing.

Also, according to the invention, said model inference module single tooth findings may include a pre-processing phase, in which after the CLAHE subphase there is an additional single tooth clipping subphase, which, for each tooth present in the X-Ray, clips the area of the original image containing the tooth.

Still according to the invention, said tooth model inference module may include a post-processing phase, comprising the subphases of: Class-dependent non-maximum suppression, in which, where there are two bounding boxes belonging to the same class such that they identify the same tooth, if those boxes overlap with an intersection value greater than or equal to a predefined threshold, the box with lower confidence is eliminated; application of the BLP model, in which constraints are placed on tooth ordering; mask contour finding, in which the masks obtained from the model are converted into point coordinates as polygons, representing the outline of the detected feature; mask contour approximation; and subdivision, in which the polygons obtained in said mask contour approximation phase are refined.

Further according to the invention, said anatomical model inference module may include a post-processing phase, comprising the subphases of: Non-maximum suppression or suppression of non-maximums, in which, where there are two bounding boxes, if said boxes overlap with an intersection value greater than or equal to a predefined threshold, the box with lower confidence is eliminated; mask contour finding, in which the masks obtained from the model are converted to point coordinates, as polygons representing the outline of the detected element mask contour approximation; subdivision, in which the polygons obtained in said mask contour approximation phase are refined; and root invasion finding, in which it is detected if there are parts of the tooth invading the maxillary sinuses or mandibular canals harbouring the inferior alveolar nerves.

Advantageously according to the invention, said inference module for the model of findings in the mouth may include a post-processing phase, comprising the subphases of: Class-dependent non-maximum suppression or suppression of class-dependent non-maximums, in which, where there are two bounding boxes belonging to the same class such that they identify the same finding, if those boxes overlap with an intersection value greater than or equal to a predefined threshold, the box with lower confidence is eliminated; non-maximum suppression or suppression of non-maximums, in which, where there are two bounding boxes, if said boxes overlap with an intersection value greater than or equal to a predefined threshold, the box with lower confidence is eliminated; mask contour finding, in which the masks obtained from the model are converted to point coordinates as polygons representing the outline of the detected feature; mask contour approximation; and subdivision, in which the polygons obtained in said mask contour approximation phase are refined.

Preferably according to the invention, said post-processing phase of the model inference module for findings on a single tooth may include the subphases of: Class-dependent non-maximum suppression or suppression of class-dependent non-maximums, in which, where there are two bounding boxes belonging to the same class such that they identify the same finding, if said boxes overlap with an intersection value greater than or equal to a predefined threshold, the box with lower confidence is eliminated;

The subphase of non-maximum suppression or suppression of non-maximums for some classes of findings in which, where there are two bounding boxes of elements belonging to classes that cannot share the same area, if those boxes overlap with an intersection value greater than or equal to a predefined threshold, the box with lower confidence is eliminated; the subphase of mask non-maximum suppression or suppression of non-maximum masks based on intersection over minimum area (class-independent) for some classes of findings, to eliminate findings that are also partially contained in others and cannot share the same area; the mask outline detection subphase, in which the masks obtained from the model are converted into point coordinates as polygons representing the outline of the detected feature; the mask outline approximation subphase; the subdivision subphase, in which the polygons obtained in said mask outline approximation phase are refined; the out-of-area tooth element removal subphase, in which where there is the outline of a tooth, if a detection is out of the area bordered by the outline, it is removed; the short root canal cure check subphase, to indicate the presence of root canal cures that are too short; and the missing internal screw check subphase, in which it is checked whether an implant lacks an internal screw.

Also, according to the invention, said method may include an operational learning phase, comprising the following phases: acquiring X-Ray images; acquiring notes associated with said X-Ray images; and performing at least one learning procedure, for the detection of features.

Still according to the invention, said phase of performing at least one learning procedure may include one or more of the following subphases: Performing an anatomical learning procedure for anatomical parts finding; performing teeth learning procedure for teeth finding; performing a mouth findings learning procedure for mouth-level findings; and performing a tooth findings learning procedure for tooth-level findings.

Advantageously according to the invention, said learning procedures can be performed in parallel.

Further according to the invention, each of said learning procedures may generate as output one or more models having as output for each detected element: A confidence vector; a label, representing the highest confidence class of the detected element; an object area bounding box; and a matrix of values, preferably real $m_{ij} \in [0, 1]$, where the value of each component $m_{ij}$ represents the confidence that the pixel on the row i column j belongs to the detected class.

Still according to the invention, said at least one learning procedure may include the following subphases: Filtering incomplete notes; randomly flipping with respect to a horizontal axis, preferably with a probability of 0.5; randomly rotating, preferably with a probability of 0.7; adjusting random contrast, in which the contrast of images is adjusted by a random factor within a range, as between [0.7, 1.3]; adjust random brightness (1335), in which you adjust the brightness of images by a random factor within a range, such as between [−0.2, 0.2]; and resize images.

Still according to the invention, said tooth model learning procedure may include the following subphase: Synthetic endoral generation, to obtain periapical and bitewing-like X-Ray images from orthopanoramics.

Advantageously according to the invention, said notes may include, for each element, a label suitable for identifying the class to which the reference element belongs, a series of points defining the polygonal outline of said element, and a bounding box within which the element is contained.

Further according to the invention, said operational phase of learning and said operational phase of inference can be alternated in time.

It is also desired by the present invention to create a system for analysing X-Rays, particularly oral X-Rays, comprising a logical processing unit having an input port for acquiring X-Rays, and an interface unit, for detecting and displaying processing results, characterized by the fact that said logical processing unit performs the method of analysing X-Rays as defined above.

BRIEF DESCRIPTION OF THE FIGURES

The present invention will now be described by way of illustration but not limitation, according to its preferred forms of embodiment, with special reference to the figures in the attached drawings, in which.

DETAILED DESCRIPTION

In the various figures, similar parts will be indicated by the same numerical references.

In general terms, it is possible to distinguish in the method of X-Ray analysis according to the present invention, two distinct operating modes or operational phases of the system for the analysis of oral X-Ray pictures (referring to FIGS. 1 and 3):

Learning 1; and

Inference 2.

Typically, when the method is in learning mode, machine learning models are generated, providing as input to the learning algorithms (better specified below) a set of X-Ray images accompanied by notes. For clarity in what follows, an annotation about an element in an image consists of three main components:

A label that identifies the class to which the referenced element belongs;

a series of points defining the polygonal outline of that element; and a bounding box within which the element is contained.

Once the operational phase 1 for learning is completed, the trained models are used and processed through inference operational phase 2. In this inference operational phase 2, the X-Ray analysis method receives incoming X-Ray images, even those never previously acquired, and detects the elements in them, as better defined below.

Preferably, said two modes of operation 1 and 2 are alternated over time to have models that are always up to date, so as to reduce detection errors committed by the method.

Discussed below are the different phases of the system's method of operation for analysing oral X-Ray pictures, divided into said two indicated modes of operation.

Learning (Training)

Figure 1:
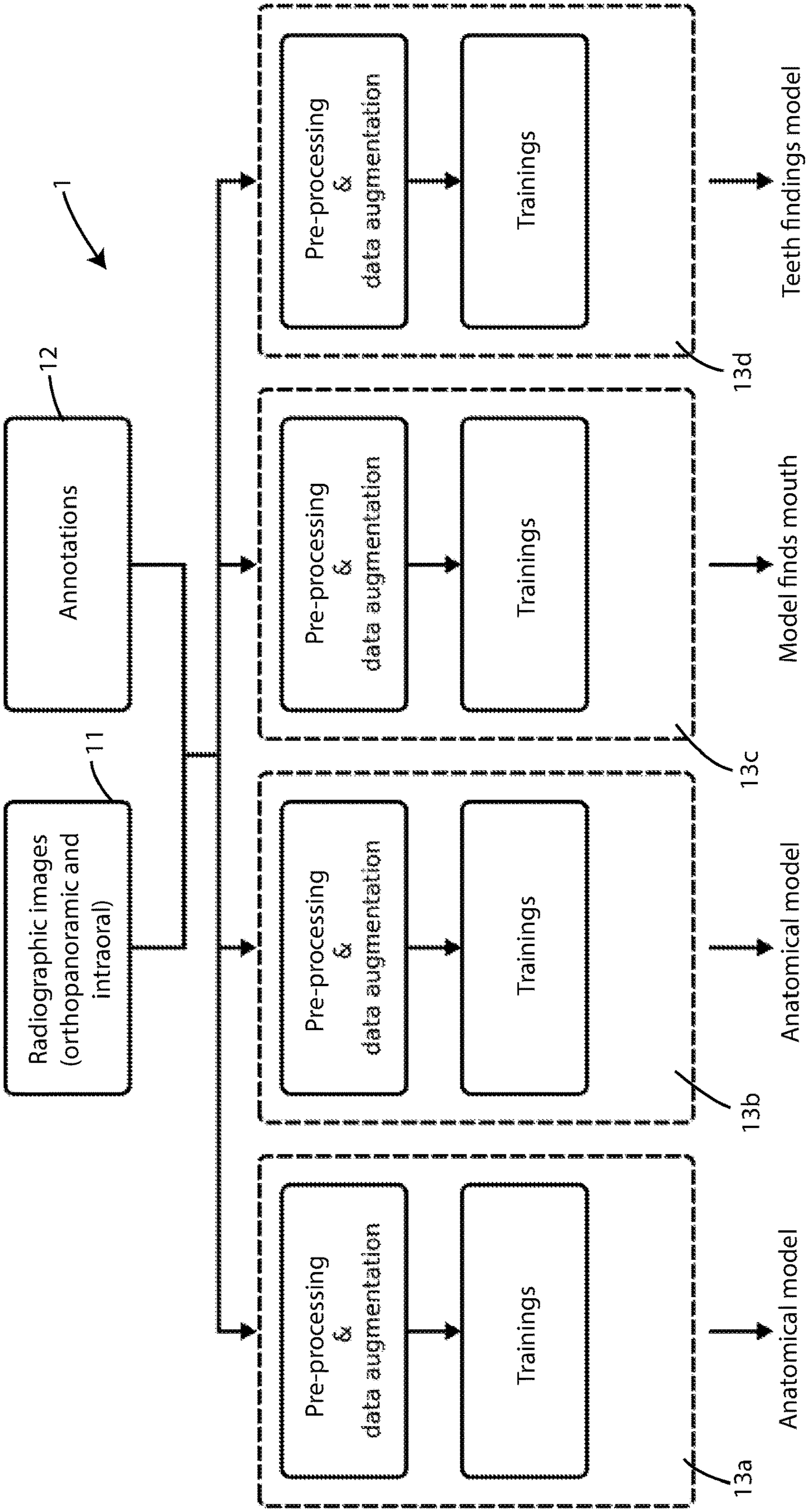
FIG. 1 shows the essential phases of a system process for analysing oral X-Ray pictures when operating in the learning (training) mode of the four models contained in the system.

With reference to FIG. 1, the main phases of the method for analysing oral X-Ray pictures when performing said learning operational phase 1 are illustrated.

Learning operational phase 1 acquires incoming X-Ray images 11 and notes 12, structured in the terms indicated above, related to the images acquired in phase 11 and, for each model to be learned, performs one or more learning procedures, such as an anatomical learning procedure 13*a*, a tooth learning procedure 13*b*, a mouth findings learning procedure 13*c* and a tooth findings learning procedure 13*d*.

For each procedure developed, a pre-processing phase and a data augmentation phase are performed, after which the actual learning (training) of the model is carried out.

A total of 300 orthopanoramics and 200 endorals (bitewing and periapical), taken by different X-Ray machines on various patients of different ages, were used for the setup of the learning procedures.

The notes were made manually by a mixed team consisting of two groups: a first group of 8 assistants (non-dentists) trained to recognize teeth and other anatomical parts, and a second group consisting of 2 experienced dentists.

The annotation process consists of defining the outlines and classes of the various recognizable elements in the X-Ray images and has been divided into two main phases.

In the first phase, the team of assistants worked to define the templates of teeth, mandibular condyles, maxillary sinuses and mandibular canals that house the lower alveolar nerves. In the second phase, the group of experienced dentists checked and, if necessary, corrected the notes made in the previous phase, after which they defined the outlines of additional elements that are recognizable only by experts (caries, fillings, pathologies, etc.).

In this context, learning means to appropriately calibrate the parameters of the four deep learning models of the proposed system in order to minimize the cost functions.

In a form of embodiment of the present invention, all models were built using a Mask Region-based Convolutional Neural Network (Mask R-CNN) architecture (He & Georgia Gkioxari, 2017). R-CNN masks have a structure divided into two phases. The first phase is called Region Proposal Network (RPN), and it scans the image. Said first phase also generates proposals (boxes that can contain an object). In the second phase, the sizes and positions of the proposals generated by the previous phase are refined, and bounding boxes and final masks are generated.

The implementation used by the Mask R-CNN model in an implementation of the invention is that provided by the model zoo of the TensorFlow Object detection APIframework (https://github.com/tensorflow/models/blob/master/research/object_fi nding/g3doc/tf2_finding_zoo.md). The above framework was used during the learning phase.

Each of the four Mask R-CNN neural network models has a specific function:

Anatomical learning procedure 13*a* is devoted to learning the model that deals with the detection of certain anatomical parts. In particular, it is concerned with surveying the contours of the mandibular condyles, mandibular canals that house the inferior alveolar nerves, and maxillary sinuses;

teeth learning procedure 13*b* is devoted to learning the model that is responsible for detecting the tooth templates (natural or artificial);

Mouth Findings Learning Procedure 13*c* is devoted to learning the model that deals with mouth-level findings, i.e., it detects the outlines of elements that cannot be associated with a single tooth, such as, for example, titanium joints or piercings (which cannot be associated with any tooth) or splints (involving multiple teeth); and Tooth findings learning procedure 13*d* is meant to learn the model that deals with the detection of the outlines of single-tooth findings, such as a cavity or filling.

The output of each of the four listed learning procedures consists of the anatomical models, teeth, mouth findings, and tooth findings, which will form the basis of the inference modules of the inference mode of operation 2 of the method according to the invention, which is described below.

The output of each model is a set of findings, where each detection is composed of four main components, as listed below:

The confidence vector, where the element no. j represents the confidence that the detected element belongs to class j;

the label/class (label), which represents the highest confidence class of the detected element;

the bounding box, which is the rectangle that delimits the area of the object; and the mask, which is a matrix of real values $m_{ij} \in [0, 1]$, where the value of each component $m_{ij}$ represents the confidence that the pixel on the row i column j belongs to the detected class.

Pre-Processing in Learning

Figure 2:
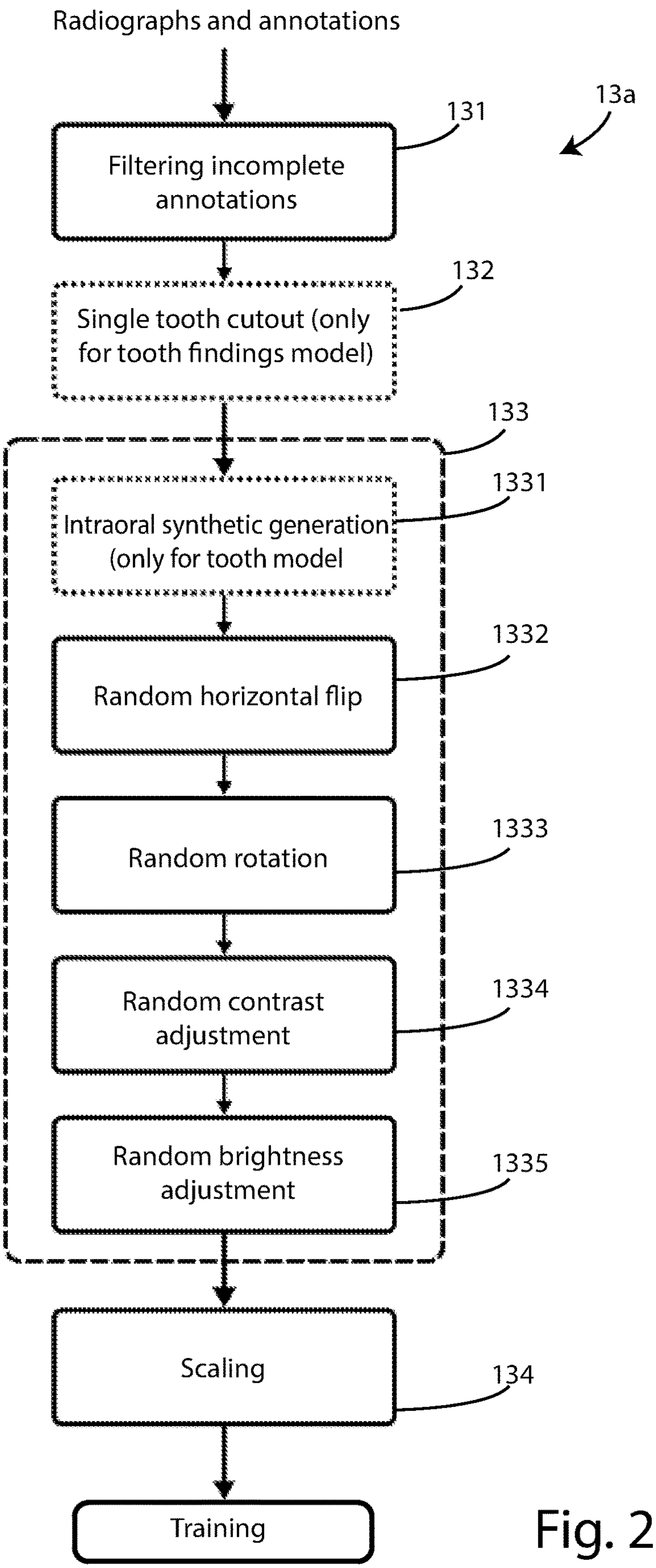
FIG. 2 shows the pre-processing and data augmentation phases performed in the learning operation mode for each model.

The pre-processing and data augmentation phases used in learning operation mode 1 are shown graphically in FIG. 2. Specifically, the following phases are carried out for each of the four models (these phases are described for anatomical learning procedure 13*a*, but are similar, unless otherwise indicated, for tooth learning procedures 13*b*, mouth findings 13*c*, and tooth findings 13*d*):

Filtering incomplete notes (subphase 131), in which X-Ray images that are not fully annotated are filtered together with the relevant notes. In addition, only those notes related to the elements to be identified by the procedure to be learned are selected;

Single tooth clipping (subphase 132; performed only while learning the tooth findings procedure). The tooth findings model detects the outlines of elements present on a tooth, so for each annotation related to a tooth the original image is cropped into a rectangle containing only the reference tooth entirely. Consequently, only those notes related to the elements on the tooth that are to be detected by the model for single-tooth findings are selected;

Synthetic endoral generation (subphase 1331; performed only during tooth model learning). It is one of the subphases of data augmentation (phase 133) that creates periapical and bitewing-like X-Ray images by appropriately cropping the orthopanoramics and, consequently, selecting the notes that fall within the cropping done;

Random horizontal flipping (subphase 1332), in which annotated images are flipped horizontally at random with a probability of 0.5. If an image is selected to be flipped horizontally, the notes used by the 13*b* tooth and anatomical 13*a* learning procedure are appropriately re-labelled so that right elements become left elements and vice versa. For example, in the case of tooth model learning, if an image is flipped, then an annotation related to tooth "17" as per FDI (Fédération Dentaire Internationale) numbering is labelled as related to tooth "27."

Random rotation (subphase 1333), in which each image and its notes can undergo rotation with probability 0.7. If an annotated image is selected for rotation, 1 to 10 images are generated obtained by rotating the original image by an angle $\alpha$, where $\alpha \in [-10°, +10°]$ for the appredriction of the tooth findings model, while $\alpha \in [-30°, +30°]$ for all other models;

Random contrast adjustment (subphase 1334), in which the contrast of images is adjusted by a random factor with a value between [0.7, 1.3];

Random brightness adjustment (subphase 1335), in which the brightness of images is adjusted by a random factor between [−0.2, 0.2]. With this subphase, date augmentation 133 ends;

Resizing (subphase 134), in which in order to allow the learning algorithms to be executed, the images must be resized so that all model parameters can be contained in memory. In some embodiments, for the model for findings on a single tooth the images are resized to the size 256×256, and for all other models to 1024×1024.

Cost Functions (Loss Function)

As mentioned above, the TensorFlow Object detection API framework (https://github.com/tensorflow/models/tree/master/research/object_finding) was exploited for the operational phase of learning 1. For all the four models shown, a so-called momentum optimizer with parameter $\alpha$=0.9 and with learning rate following the cosine decay formula with warm up (Loshchilov & Hutter, 2017) with base learning rate of 0.008 was utilized. The number of learning phases used is equal to 400.000. The cost functions (so-called loss functions) of the models used are described below.

For the first phase of Mask R-CNN, the cost function is used:

$$L_1 = \lambda_{11} \cdot L_{loc} + \lambda_{12} \cdot L_{obj}$$

where:

$\lambda_{11}$=2.0 and $\lambda_{12}$=1.0

$L_{loc}$ is the Area Proposal Network or Region Proposal Network (RPN)-localization loss (see Ren, He, Girshick, & Sun, 2015). Calculate errors in terms of size and position of proposals; and $L_{obj}$ is the RPN objectness loss (see Ren, He, Girshick, & Sun, 2015), which calculates errors due to proposals that do not contain any of the objects to be detected.

For the second phase, however, the following cost function was used:

$$L_2 = \lambda_{21} \cdot L_{loc2} + \lambda_{22} \cdot L_{cls} + \lambda_{23} \cdot L_{mask}$$

where:

$$\lambda_{21} = 2.0, \lambda_{22} = 1.0, \lambda_{23} = 4.0;$$

$L_{loc2}$ is the localization loss of the second phase (see Girshick, 2015). It allows calculation of errors in terms of size and position of bounding boxes; and $L_{cls}$ is the classification loss (see as defined in Girshick, 2015). It calculates the classification errors of the bounding boxes;

$L_{mask}$ is mask loss (as defined in He & Georgia Gkioxari, 2017). Calculates errors due to segmentation masks.

Inference

Figure 3:
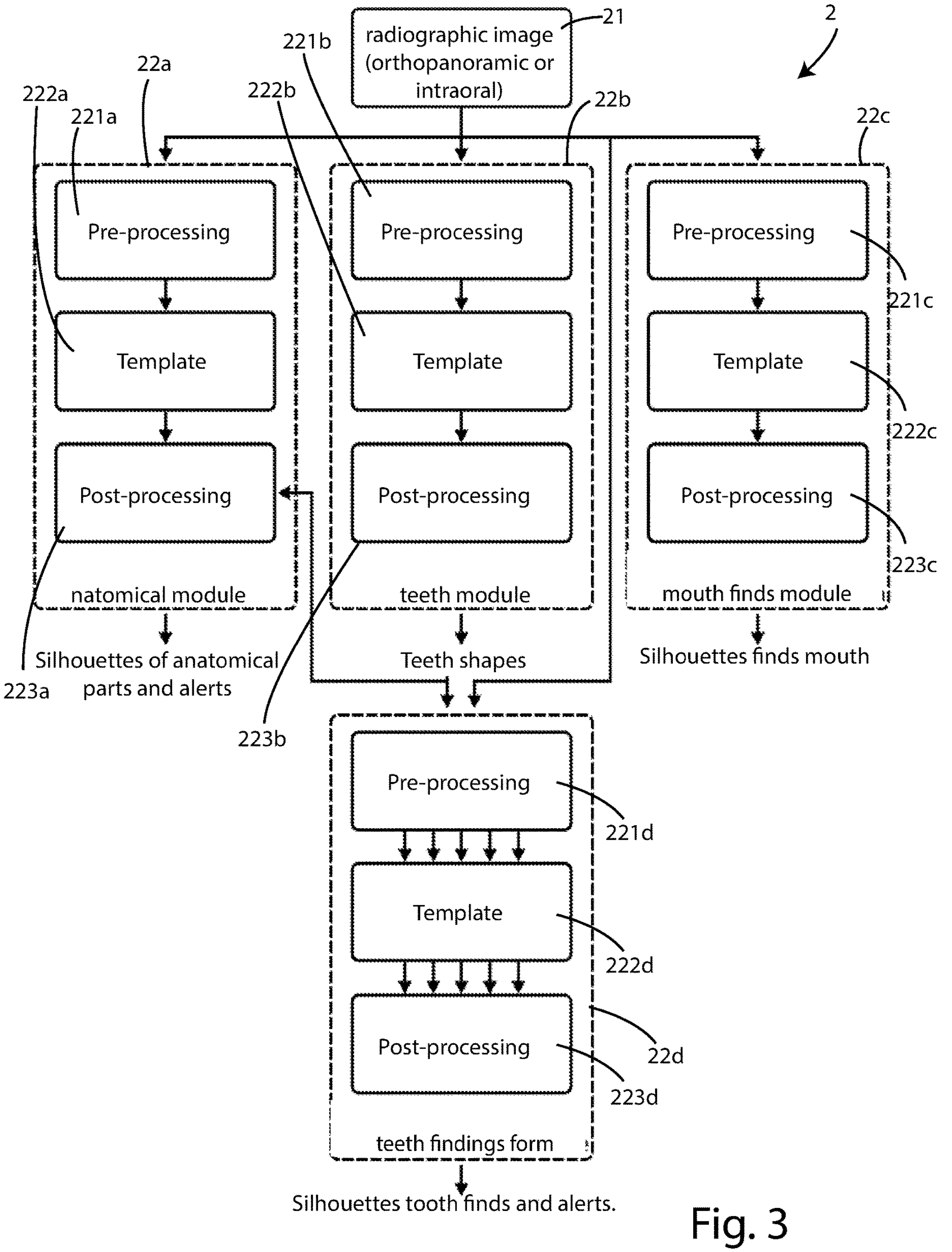
FIG. 3 shows the phases of system operation in the inference operating mode.

In inference operational phase 2, shown in general in FIG. 3, the method according to the invention receives as input an X-Ray image 21 (orthopanoramic or endoral) and in parallel the anatomical model inference module 22*a*, the teeth model inference module 22*b* and the mouth findings model inference module 22*c* are executed.

The model inference module findings on single tooth 22*d* are run in cascade with the inference module the teeth model inference module 22*b*.

The anatomical model inference module 22*a* and the inference module for the single-tooth model findings 22*d* also acquire as input the geometric coordinates that make up the tooth templates detected by the tooth model inference module 22*b*.

Specifically, the anatomical model inference module 22*a* needs the post-processing tooth templates as input in order to generate alerts; while the single-tooth findings model inference module 22*d* needs the tooth templates as input in order to appropriately crop the original input image.

All inference modules (with the exception of the inference module of the single-tooth model findings 22*d*) can be run in parallel mode.

In addition, all inference modules are divisible into three successive subphases: pre-processing 221, model inference 222 and post-processing 223.

Figure 4:
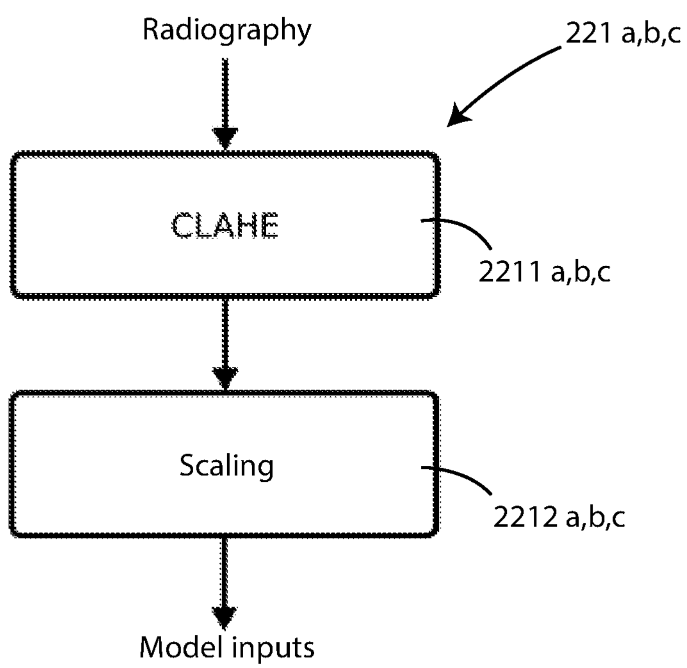
FIG. 4 shows in detail the pre-processing subphases of the inference module of tooth finding, anatomical parts and mouth-level findings.

The pre-processing phases 221*a*, 221*b*, 221*c* for the anatomical model inference module 22*a*, for the teeth model inference module 22*b*, and for the mouth findings model inference module 22*c* are shown in detail in FIG. 4.

The pre-processing phase 221 is in turn divided into two successive subphases: In the first subphase of Contrast Limited Adaptive Histogram Equalization (CLAHE) 2211 the image is modified in contrast.

In the second 2212 scaling subphase, however, the image is scaled to the size 1024×1024 to be processed by the model obtained from running the system in learning mode.

Figure 5:
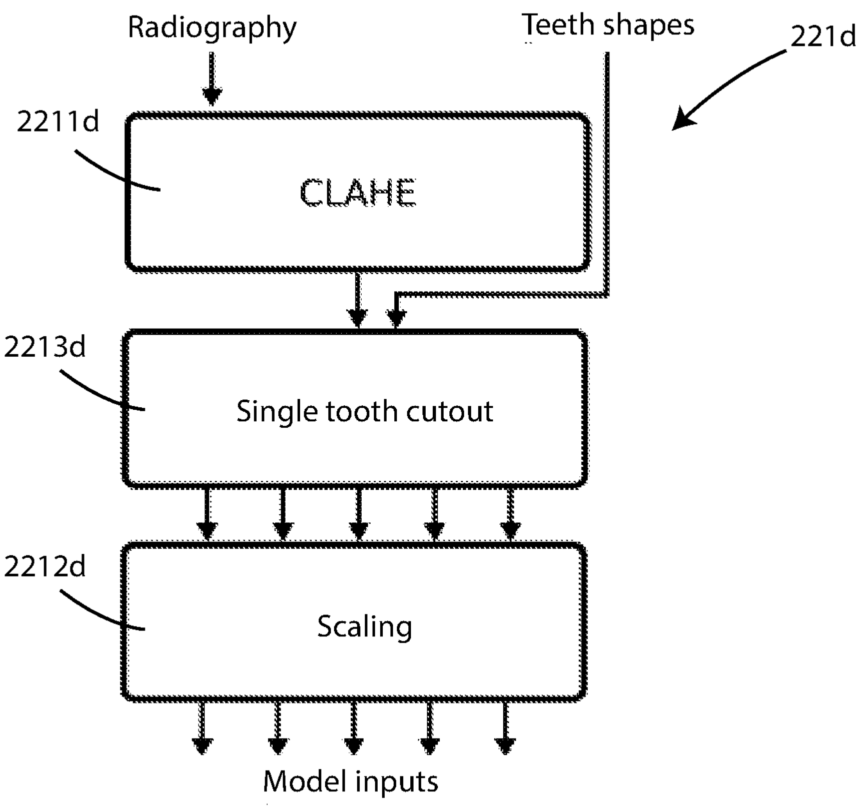
FIG. 5 shows the pre-processing subphases of the tooth-level findings inference module.

FIG. 5, on the other hand, shows in detail the 221*d* pre-processing subphases of the inference module of the single tooth 22*d* model findings. Compared with the pre-processing phase of the other inference modules, after the CLAHE 2211*d* subphase, there is an additional single tooth 2213*d* clipping subphase that, for each tooth in the radiograph, clips the area of the original image containing the tooth, resulting in as many clipped images as the number of teeth detected. To perform said single tooth 2213*d* clipping subphase, it is necessary to provide as input, in addition to the enhanced X-Ray image after the CLAHE 2211*d* subphase, the tooth templates obtained at the end of the tooth model inference module 22*b*. Finally, all cut-outs of the original image are resized to the size 256×256 in the 2212*d* resizing subphase to be processed by the model obtained in the learning operation mode.

In some embodiments, the subphase of CLAHE 2211, because it is common to all inference 22 forms, is performed only once for all inference modules.

Figure 6:
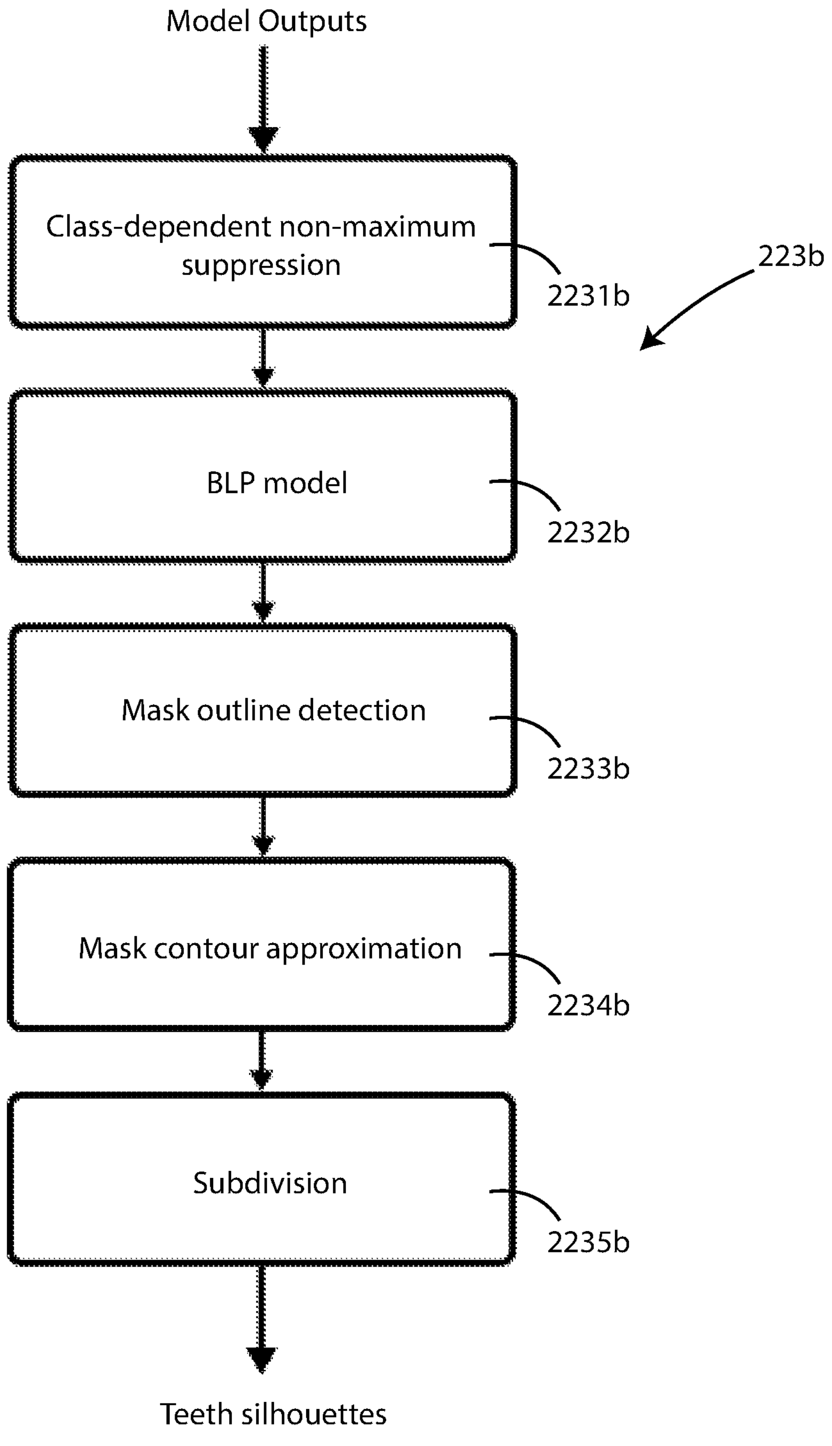
FIG. 6 shows the subphases of the post-processing phase of the tooth findings inference module in inference operation mode.
Figure 10:
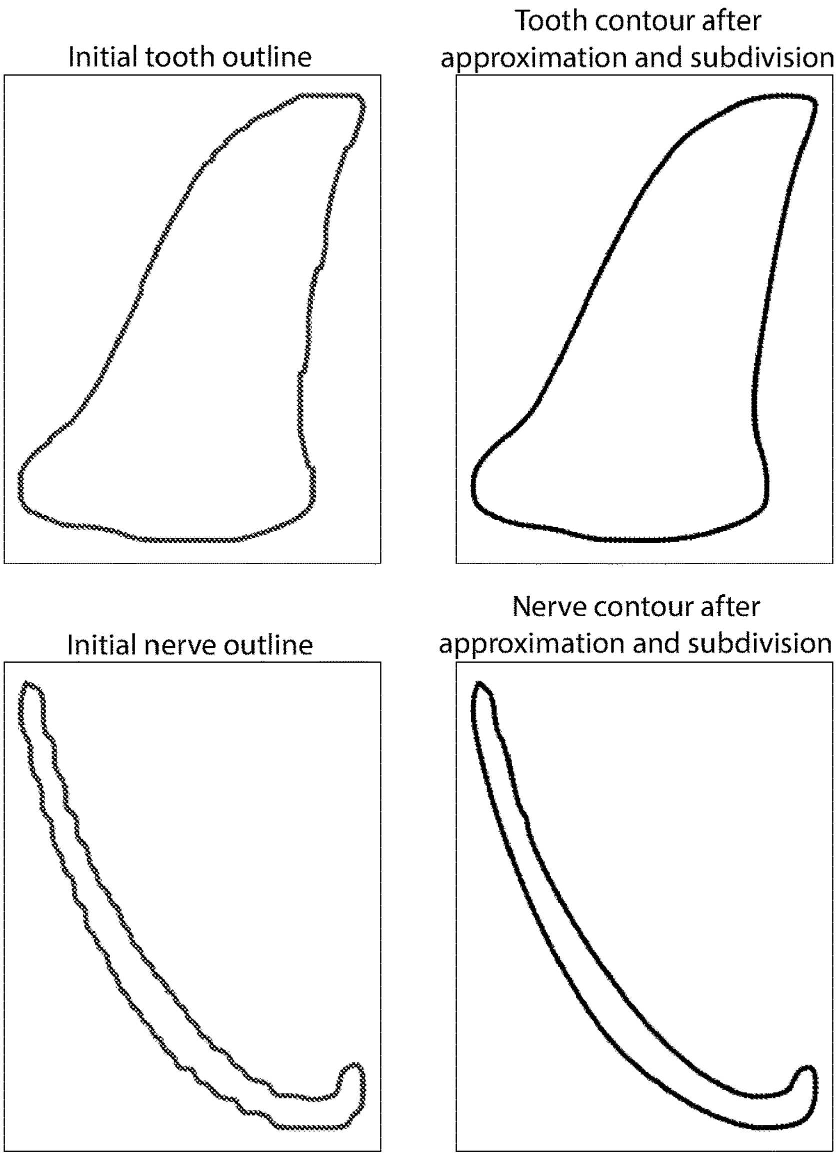
FIG. 10 shows an example of the advantages of applying the phases of "Mask contour approximation" and "subdivision"

The post-processing subphase 223*b* of the tooth model inference module 22*b* receives as input the output obtained from the tooth detection inference module. The main phases are shown in detail in FIG. 6, which are performed in succession:

- Class-dependent non-maximum suppression or suppression of class-dependent non-maximums (subphase 2231*b*): In this subphase, where there are two bounding boxes belonging to the same class, i.e., two boxes identifying the same tooth, if these two boxes overlap with an Intersection-over-Union (IoU) value greater than or equal to a certain threshold, the box with lower confidence is eliminated. The threshold value of IoU used in an embodiment was, by way of example but not as a limitation, 0.55.
- BLP model (subphase 2232*b*): In this subphase, the mathematical model in Binary Linear Programming (BLP) places constraints on the ordering of teeth. As an example, on an X-Ray it cannot be possible to have a "16" tooth that is to the right of a "13." This mathematical model allows labels to be reassigned to boxes if constraints are violated. The mathematical constraints are detailed in the next subsection.
- Mask contour detection (subphase 2233*b*): In this subphase, the masks obtained from the model are converted into point coordinates, i.e., polygons representing the outline of the detected element. The technique used is based on the defined algorithm (Suzuki & Abe, 1985). In some embodiments, the threshold value for converting masks obtained from the model to masks with binary values is 0.4.
- Mask contour approximation (subphase 2234*b*): In this subphase, the points obtained in the previous subphase may be too many and insert noise, so for each mask, the number of points is reduced using an approach based on the Douglas-Peucker algorithm.
- Subdivision (Subphase 2235*b*): In this subphase the polygons obtained in the previous subphase are refined through a subdivision phase, thus obtaining "smoother" polygons. The advantages of applying polygon approximation and subsequent subdivision are shown visually as an example in FIG. 10.

The output of this module is a list of findings each of which consists of four basic parts:

- Label/class (label): Class to which the detected item belongs.
- Confidence: Degree of confidence of class membership.
- Bounding box: A rectangle delimiting the area of the object. Each box is a vector of 4 elements of the form [$x_{min}$, $y_{min}$, width, height].

Contour: List of geometric coordinates that define the outline of a surveyed object.

Figure 12:
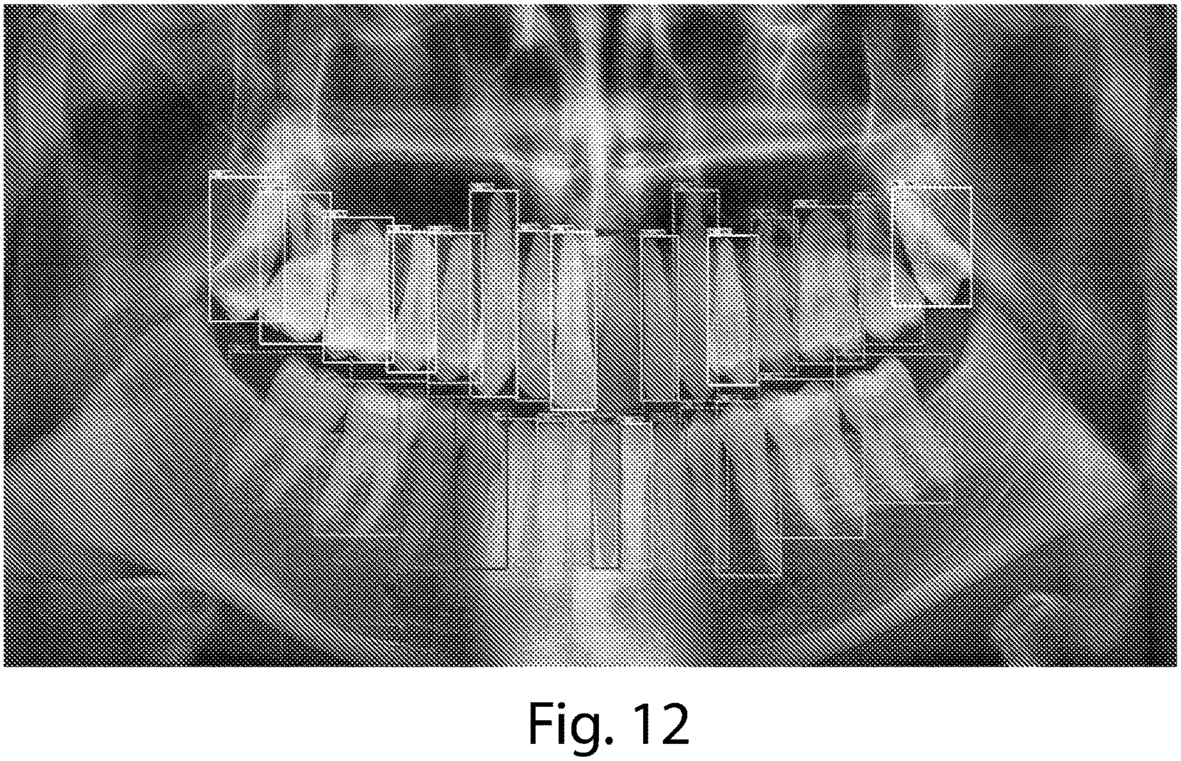
FIG. 12 shows an example of the outcome results of the tooth detection inference module in inference operation mode.

An example of the output of the tooth detection inference module is shown in FIG. 12.

BLP Model

As is well known, Mathematical Programming (MP) is a branch of operations research concerning optimization using mathematical techniques. A mathematical programming problem is defined by a set of variables, an objective function that must be minimized or maximized, and a set of constraints, expressed as equalities and inequalities, on the variables.

Mathematical programming is divided into different classes of problems, such as Linear Programming (LP), quadratic programming, convex programming, etc. Specifically, in LP, the objective function and constraints are linear, and the variables are continuous. If the variables can only have integer values, the problem is in the Integer Linear Programming (ILP) class. A special subclass of ILP problems are Binary Linear Programming (BLP) problems in which all variables are evaluated in binary mode.

A BLP problem is expressed in canonical form as follows:

Maximize $c^T x$
Subject to the constraints $Ax \le b$
$x \ge 0$
and $x \in \{0,1\}^m$ where c is the cost vector ($c^T$ is the row vector, transposed from the column vector), x is the vector of binary decision variables of dimension m, A is a matrix n×m, n is the number of constraints and m is the number of binary decision variables.

After the post-processing phase of class-dependent non maximum suppression the BLP model receives input findings, each of which consists of 4 main components:

Confidence vector: Confidence vector where the j-th element represents the confidence that the detected element belongs to class j;

Label/class (label): Class with higher confidence than the detected element;

Bounding box: A rectangle delimiting the area of the object;

Mask: A matrix of real values $m_{ij} \in [0, 1]$, where the value of each component $m_{ij}$ represents the confidence that the pixel on the row i column j belongs to the detected class.

For each arcade, these findings are ordered in ascending order according to the coordinate x and in second order to the coordinate y of the centroids of the bounding boxes. After that, again for each arcade, a G-dictionary is created that contains key-value pairs, where the key is a position, and the value is a list of the findings whose boxes are in that position. Dictionary G is created according to the following algorithm:

Input: L Findings list.
Algorithm:
1. G ← { } and pos ← 1
2. for i ranging from 0 to length(L)
  ○ H ← extractHighIoU(L[i], L[i + 1:], 0.7), where extractHighIoU (Findings, List of Findings, τ) is a function that returns the list of findings in List of Findings whose boxes have an IoU with respect to the detection box greater than or equal to τ
  ○ if among the values of G there is no superset of H
    ■ I insert the pair (pos, H) in G
    ■ pos = pos + 1
Output: G The dictionary G of an arcade is then converted into two tensors of box positions and two confidence matrices, as described below.

It is said to be the tensor of the boxes V of boundary relative to the permanent teeth of the arch of size N×M×4, where N is the number of positions and M is the number of possible classes of permanent teeth for the arch considered. Since every human being has the same number of possible classes of permanent teeth, for both the upper and lower arch M will always be equal to 16. In other words, each column is associated with a class of tooth in the arch in order from the rightmost class anatomically to the leftmost, i.e:

For the upper arch: [18, 17, 16, 15, 14, 13, 12, 11, 21, 22, 23, 24, 25, 26, 27, 28]

For the lower arch: [48, 47, 46, 45, 44, 43, 42, 41, 31, 32, 33, 34, 35, 36, 37, 38].

We shall assume here that the tooth classes respect the FDI nomenclature.

The third dimension has value 4 because a bounding box is defined by 4 values in the form [$x_{min}$, $y_{min}$, width, height].

We also consider the tensor of the bounding boxes F related to the deciduous teeth of the arch of size N×K×4, where K is the number of possible classes of deciduous teeth for the considered arch. Since human beings have the same number of deciduous teeth for both the upper and lower arch K will always be equal to 10. In other words, each column is associated with a class of tooth in the arch in order from the rightmost class anatomically to the leftmost, i.e:

Upper arch: [55, 54, 53, 52, 51, 61, 62, 63, 64, 65]

Lower arch: [85, 84, 83, 82, 81, 71, 72, 73, 74, 75]

$C_p$: Matrix N×M of confidence for classes related to permanent teeth in the arch.

$C_d$: Matrix N×M of confidence for classes related to deciduous teeth in the arch.

Tensors and matrices are constructed according to the following algorithm.

Input

G dictionary containing key-value pairs, where the key is a location, and the value is a list of findings Algorithm:
1. V ← [ ], F ← [ ], $C_p$ ← [ ], $C_d$ ← [ ]
2. For each pair (pos, findings) in G:
  ○ conf_vectors ← extract_confidence_vectors (findings); where extract_confidence_vectors extracts all confidence vectors from a list of findings and concatenates them one row after another.
  ○ boxes ← extract_boxes (findings); where extract_boxes extracts all bounding boxes from a list of findings.

-continued

- mean_conf ← mean_row_axis(conf_vectors); where mean_row_axis creates an average along the rows.
- mean_permanent_conf ← extract_permanent_columns(mean_conf); where extract_permanent_columns extracts only the columns of a confidence vector associated with the classes of permanent teeth in an arch.
- $C_p$[pos] ← mean_permanent_conf
- mean_deciduous_conf ← extract_deciduous_columns(mean_conf)
- $C_d$[pos] ← mean_deciduous_conf
- mean_box ← mean_row_axis(boxes)
- V[pos] ← repeat(mean_box, M); where repeat(v, n) is a function that returns a vector where v is repeated n times.
- F[pos] ← repeat(mean_box, K)
- For each finding in findings
    - $m_p$ ← max(mean_permanent_conf)
    - $m_d$ ← max(mean_deciduous_conf)
    - $i_p$ ← argmax(mean_permanent_conf)
    - $i_d$ ← argmax(mean_deciduous_conf)
    - If $m_p > m_d$
        - V[pos, $i_p$] ← finding.box
    - otherwise
        - F[pos, $i_d$] ← finding.box Output
- V, F, $C_p$, $C_d$ The mathematical model was developed by exploiting the OR-Tools optimization library (https://developers.google-.com/optimization).

For each set of findings belonging to an arcade, a BLP model is defined according to the mathematical definition below.

Input

Let N be the number of possible box positions.

$C_p$: Matrix N×M of confidence for the classes related to the permanent teeth in the arch, obtained by concatenating the confidence vectors of the ordered findings.

$C_d$: Matrix N×M of confidence for classes related to deciduous teeth in the arch.

Tensor of the bounding boxes V related to the permanent teeth of the arch.

Tensor of the bounding boxes F related to the deciduous teeth of the arch.

Variables

The binary variables in the model are as follows:

The matrix of permanent teeth P of size N×M. In particular, if $p_{ij}=1$ then at position i there will be a permanent class tooth associated with the column j. For example, if $p_{2,3}=1$ and you are considering the upper arch, then at position 2 there will be a class 16 tooth.

The matrix of deciduous teeth D of size N×K. In particular, if $d_{ij}=1$ then at position i there will be a deciduous tooth of the class associated with the column j. For example, if $d_{2,3}=1$ and you are considering the lower arch, then at position 2 there will be a class 83 tooth.

The vector of supernumeraries s of size M, where M is the number of possible classes of permanent teeth for the considered arch (M=16). Each position of the elements of the vector is associated with the class of a tooth in the arch in order from the rightmost class anatomically to the leftmost, i.e:

For the upper arch: [18, 17, 16, 15, 14, 13, 12, 11, 21, 22, 23, 24, 25, 26, 27, 28];

For the lower arch: [48, 47, 46, 45, 44, 43, 42, 41, 31, 32, 33, 34, 35, 36, 37, 38].

Specifically, if $s_j=1$ then there will be two permanent teeth of the same class associated with the position j. For example, if $s_4=1$ and you are considering the upper arch, then two class 15 teeth will be present.

Constraints

They can be divided into constraints in three classes: Quantity constraints; horizontal axis sorting constraints; and vertical axis sorting constraints.

Quantity Constraints

Constraint 1). At a given position there can be only one tooth between permanent and deciduous:

$$\forall_i \sum_{j=1}^{M} p_{ij} + \sum_{j=1}^{K} d_{ij} \le 1 \text{ with } i \in \{1, \cdots, N\}$$

Constraint 2). A maximum of two permanent teeth can belong to the same class or, in other words, there can be a maximum of one supernumerary in each class of teeth:

$$\forall_j \sum_{i=1}^{N} p_{ij} \le 2 \text{ with } j \in \{1, \cdots, M\}$$

Constraint 3). For deciduous teeth there cannot be two teeth belonging to the same class:

$$\forall_j \sum_{i=1}^{N} d_{ij} \le 1 \text{ with } j \in \{1, \cdots, K\}$$

Constraint 4). Relates the variables of the matrix P with that of the vector s:

$$\forall_j \sum_{i=1}^{N} p_{ij} \leq 1 + s_j \text{ with } j \in \{1, \cdots, M\}$$

Sorting Constraints on the Horizontal Axis

Constraint 5). If at the position i there is a permanent tooth of the j-th class, there cannot be permanent teeth with a class lower than the j-th in positions subsequent to i:

$$\forall_i \forall_j \forall_t \forall_h\, p_{th} \leq 1 - p_{ij} \text{ with } i \in \{1, \cdots, N-1\},$$
$$j \in \{1, \cdots, M\}, t \in \{i+1, \cdots, N\}, h \in \{1, \cdots, j-1\}$$

Constraint 6). Similar to the previous one, if at the position i there is a deciduous tooth of the j-th class, there cannot be deciduous teeth with class lower than the j-th in positions subsequent to i:

$$\forall_i \forall_j \forall_t \forall_h\, d_{th} \leq 1 - d_{ij}$$
$$\text{with}$$
$$i \in \{1, \ldots, N-1\}, j \in \{1, \ldots, K\}, t \in \{i+1, \ldots, N\}, h \in \{1, \ldots, j-1\}$$

Constraint 7). If at position i there is a permanent tooth of class j-th, then all variables associated with boxes that have value $x_{min}<v_{ij0}$ must have value 0, where $v_{ij0}$ represents the value $x_{min}$ of the box $v_{ij}$ within the matrix V.

$$\forall_i \forall_j\, Sum(SelectPrevBoxNextPos(P, V, i)) \leq 1 - p_{ij}$$
$$\text{with}$$
$$i \in \{1, \ldots, N-1\}, j \in \{1, \ldots, M\}$$

The function SelectPrevBoxNextPos(P,V,i) returns the matrix variables P of rows from i+1 to N that are associated with boxes that have value $x_{min}<v_{ij0}$.

Constraint 8). Similar to previous, if at the position i there is a deciduous tooth of the j-th class, then all variables associated with boxes that have the value $x_{min}<f_{ij0}$ must have value 0, where $f_{ij0}$ represents the value $x_{min}$ of the box $f_{ij}$ within the matrix F.

$$\forall_i \forall_j\, Sum(SelectPrevBoxNextPos(D, F, i)) \leq 1 - d_{ij}$$
$$\text{with}$$
$$i \in \{1, \ldots, N-1\}, j \in \{1, \ldots, K\}$$

Sorting Constraints on the Vertical Axis

Constraint 9). It is not possible for two permanent teeth to be under each other and belong to the same class c, where c∈[15, 14, 13, 12, 11, 21, 22, 23, 24, 25] for the upper arch (while c∈[45, 44, 43, 42, 41, 31, 32, 33, 34, 35] for the lower arch).

First, the set of variables is calculated B:

for the upper arch $$\forall_i \forall_j\, B \leftarrow BelowBoxes(P, V, v_{ij}, j)$$

for the lower arch $$\forall_i \forall_j\, B \leftarrow AboveBoxes(P, V, v_{ij}, j)$$

The function BelowBoxes(P,V,$v_{ij}$,h) (AboveBoxes(P,V, $p_{ij}$,h)) returns all those variables in the column h of P associated with those boxes that are below (above) the box $v_{ij}$.

After that, constraints are imposed:

$$\forall_{b \in B}\, b \leq 1 - p_{ij}$$
$$\text{with}$$
$$i \in \{1, \ldots, N\}, j \in \{4, \ldots, M-3\}$$

Constraint 10). If we are in the upper (lower) arch and below (above) a permanent tooth there are no findings of other teeth, there can be no deciduous teeth corresponding to the class of the permanent tooth.

First, the set of variables is calculated B:

For the upper arch $$\forall_i \forall_j\, B \leftarrow BelowBoxes(D, F, v_{ij}, j-3)$$

For the lower arch $$\forall_i \forall_j\, B \leftarrow AboveBoxes(D, F, v_{ij}, j-3)$$

If B is empty, then constraints are imposed:

$$B = \emptyset \Rightarrow \forall_t\, d_{t,j-3} \leq 1 - p_{ij}$$
$$\text{With}$$
$$t \in \{1, \ldots, N\} \text{ and } i \in \{1, \ldots, N\}, j \in \{4, \ldots, M-3\}$$

Constraint 11). If there are two boxes detected one below the other and we are in the upper (lower) arch, it is not possible for the deciduous tooth to be above (below) the permanent tooth.

First, the set of variables is calculated B:

For the upper arch $$\forall_i \forall_j\, B \leftarrow BelowBoxes(P, V, f_{ij-3}, j)$$

For the lower arch $$\forall_i \forall_j\ B \leftarrow AboveBoxes(P, V, f_{ij-3}, j)$$

and constraints are imposed:

$$\forall_{b \in B}\ b \leq 1 - d_{ij-3}$$

with $$i \in \{1, \ldots , N\},\ j \in \{4, \ldots , M-3\}$$

Objective Function

The objective function to be maximized is as follows:

$$\lambda_1 \|C_p P\|_2^2 + \lambda_2 \|C_d D\|_2^2 + \lambda_3 \|P\|_2^2 + \lambda_4 \|D\|_2^2 - \lambda_5 \|S\|_2^2$$

Where:

- In an embodiment $\lambda_1=1.0$, $\lambda_2=1.0$, $\lambda_3=0.5$, $\lambda_4=0.5$ e $\lambda_5=0.7$;
  - The first and second contributions are used to maximize the use of higher confidence tooth classes.
  - The third and fourth contributions are used to maximize the absolute number of permanent and deciduous teeth, respectively.
  - The last contribution is a subtrahend used to try to minimize the absolute number of supernumerary teeth.

Post-Processing for the Anatomical Model Inference Module

Figure 7:
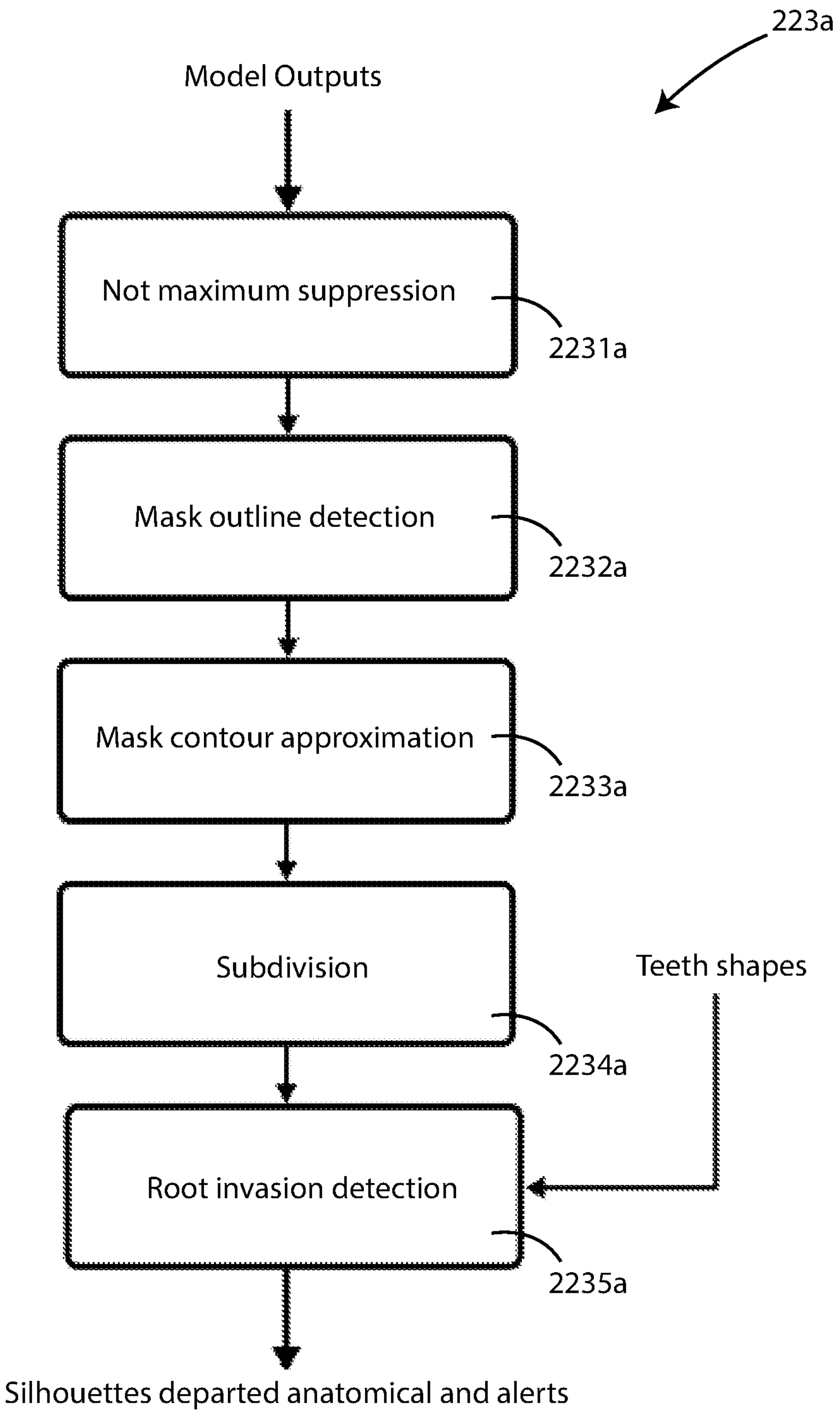
FIG. 7 shows the post-processing subphases of the anatomical parts inference module in inference operation mode.

The post-processing phase 223*a* of the anatomical model inference module 22*a* receives as input the output obtained from the execution of the anatomical model 222*a*. Its main phases are shown in detail in FIG. 7 and are performed in succession. Specifically said phases include:

- The subphase of non-maximum suppression or suppression of non-maximums 2231*a* (class-independent), in which there are two bounding boxes, and if these two boxes overlap (regardless of class) with an Intersection-over-Union (IoU) value greater than or equal to a certain threshold, the box with lower confidence is eliminated. In some embodiments, the threshold value of IoU used is 0.5;
- Subphase mask contour detection 2232*a*. In some embodiments, the threshold value for conversion to binary masks is 0.4;
- Subphase mask contour approximation 2233*a*.
- Subdivision subphase 2234*a;*
- Root invasion detection subphase 2235*a*, in which it is detected whether there are any tooth parts invading the maxillary sinuses or mandibular canals harbouring the inferior alveolar nerves; consequently, it needs the list of detected tooth templates as input. For each tooth detected and for each anatomical part that may be affected by root invasion of a tooth (a maxillary sinus or mandibular canal hosting a lower alveolar nerve), the following formula is calculated:

$$\alpha = \frac{\text{Area of Tooth} \cap \text{Area of Anatomical Part}}{\text{Area Tooth}}$$

- If $\alpha \geq \tau$ then it is reported that the tooth invades the anatomical part. In some embodiments, the threshold value $\tau$ is set to 0.1.

The output of the post-processing phase 223*a* of the anatomical model 22*a* inference module is a list of findings (each consisting of label, confidence, bounding box, and outline) and a list of alerts indicating whether there are roots belonging to a tooth invading a mandibular canal that houses an inferior alveolar nerve or a paranasal sinus.

Figure 13:
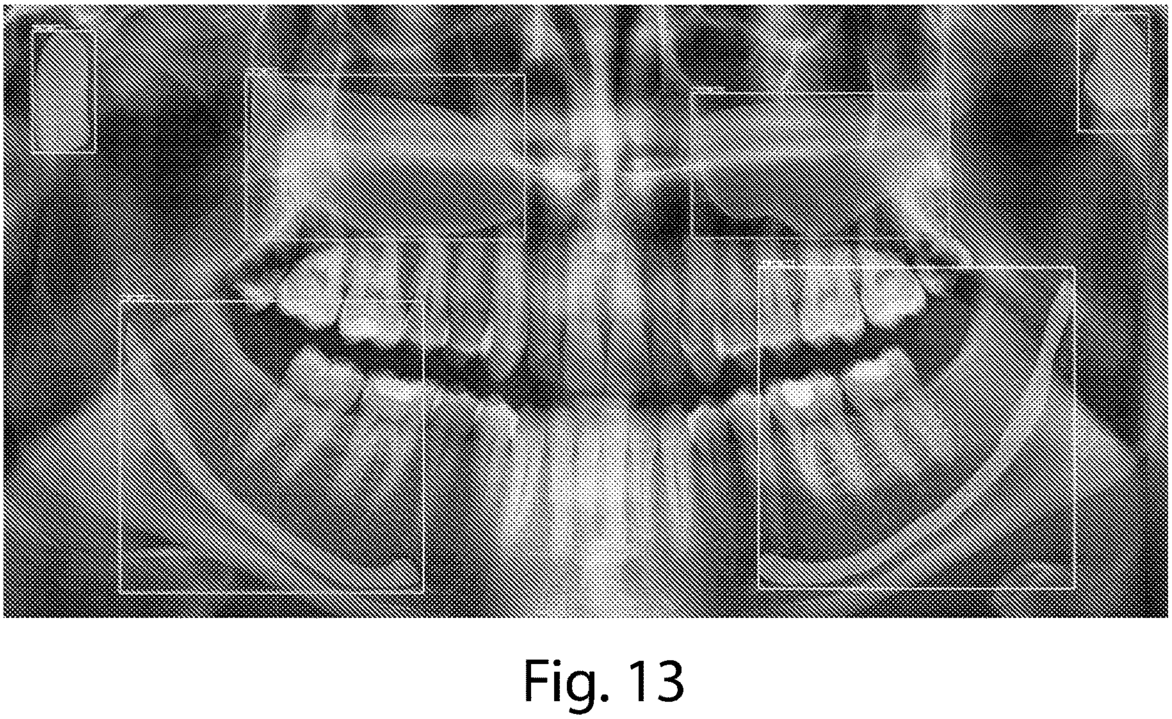
FIG. 13 shows an example of the outcome results of the anatomical part detection inference module in the inference operation mode.

A visual example of the findings obtained from the output of the inference module for the detection of anatomical parts is shown in FIG. 13.

Post-Processing for the Inference Module of the Mouth-Level Findings Model

Figure 8:
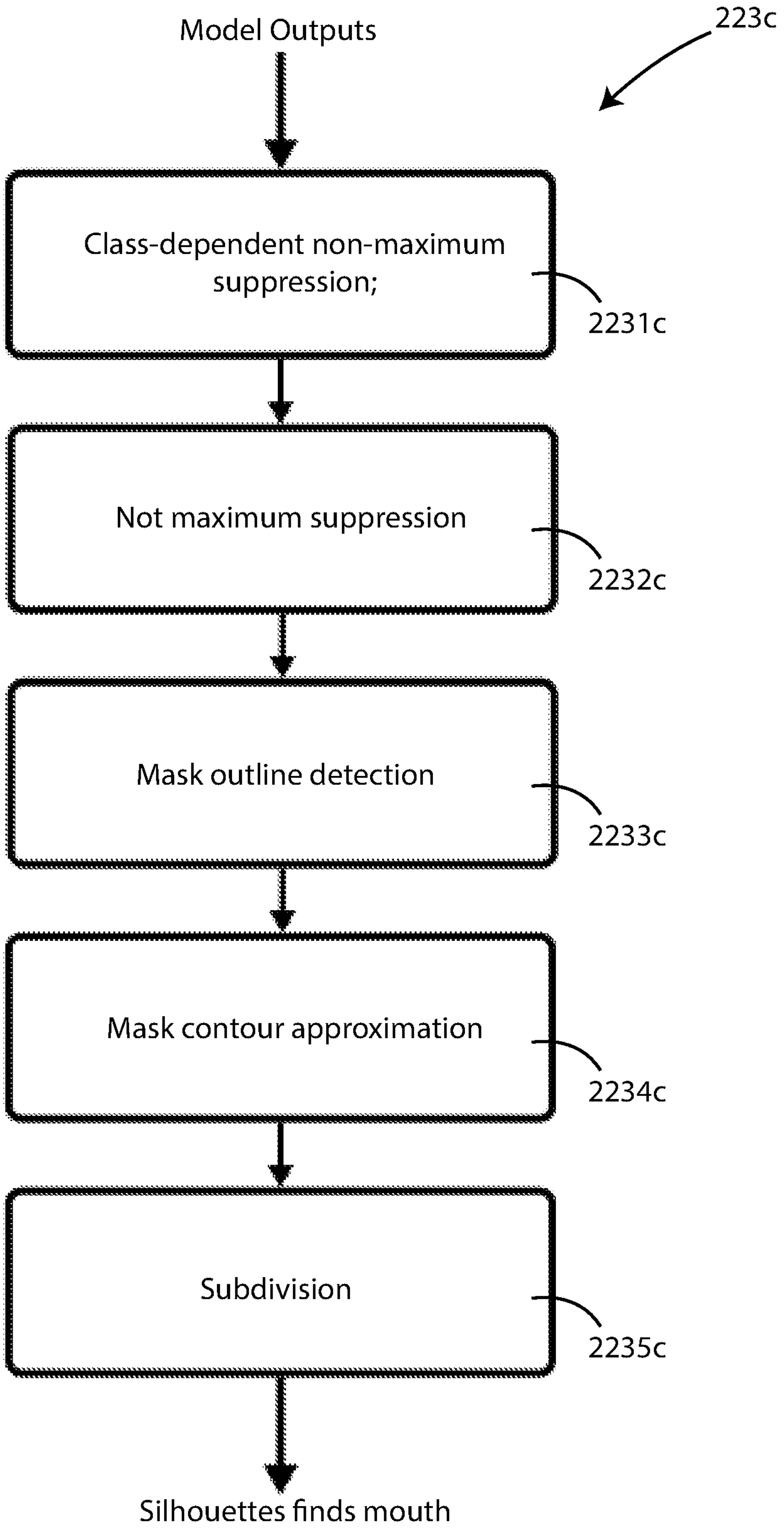
FIG. 8 shows the post-processing subphases in inference mode of the mouth-level findings inference module.

The post-processing phase of the inference module for mouth-level findings receives as input the output obtained from the execution of the mouth 222*c* model findings. Its main phases are shown in detail in FIG. 8. The subphases of this procedure are performed in succession:

- Subphase of class-dependent non-maximum suppression or suppression of class-dependent non-maximums 2231*c*, in which, in some embodiments, the IoU threshold value used is 0.6;
- Subphase of non-maximum suppression or suppression of non-maximums 2232*c* (class-independent), in which the IoU threshold value used, in some embodiments, is 0.9;
- Subphase of mask contour detection 2232*c* or post-processing. The threshold value for conversion to binary masks is 0.4;
- Subphase of mask contour approximation 2234*c;*
- Subphase of Subdivision 2235*c*.

The output of this procedure is a list of findings (each consisting of label, confidence, bounding box and outline).

Figure 9:
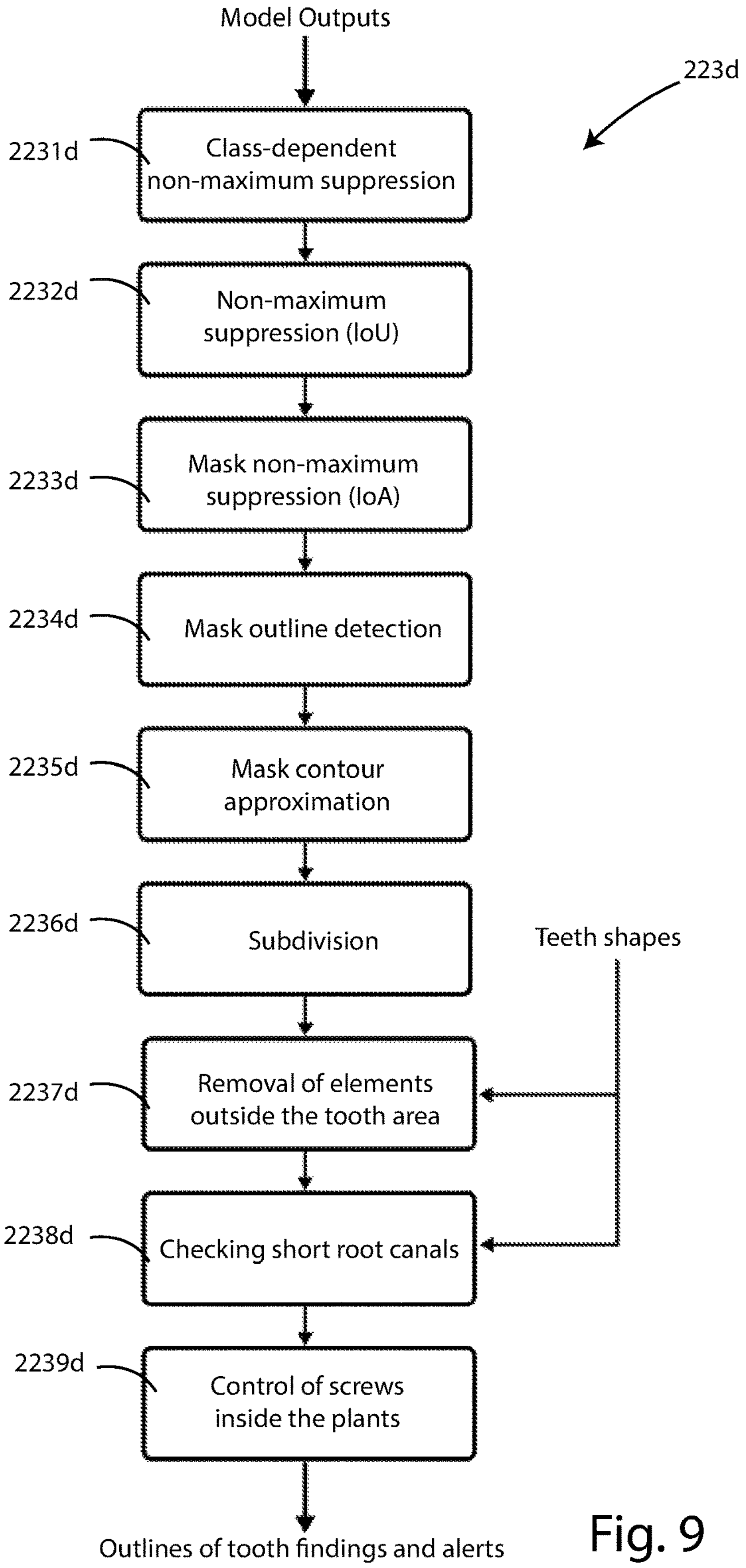
FIG. 9 shows the post-processing subphases of the inference module of tooth-level findings finding.

Post-Processing for the Detection Inference Module at the Individual Tooth Level The 223*d* post-processing phase of the single tooth 22*d* findings model inference module receives as input the output obtained from the execution of the 222*d* tooth findings model. Its main phases are shown in detail in FIG. 9. The subphases of this procedure are performed in succession:

- The subphase of class-dependent non-maximum suppression or suppression of class-dependent non-maximums 2231*d*, with a IoU threshold value used in some embodiments of 0.6;
- The subphase of non-maximum suppression or suppression of non-maximums 2232*d* (class-independent), where in some embodiments the threshold value of IoU used is 0.9. This is not done for all findings, but only for those that are mutually exclusive (e.g., a pixel area cannot be associated with both a filling and a root canal treatment, while it can belong to both a banding and a filling);
- The subphase of mask non-maximum suppression or suppression of non-maximum masks based on the intersection on minimum area (class-independent) 2233*d*, where the goal of this phase is to eliminate those findings that are (partially) contained in others.
- Where two masks exist, the following formula is calculated:

$$\beta = \frac{AreaMask_1 \cap AreaMask_2}{\min(AreaMask_1, AreaMask_2)}$$

If β≥τ then the detection with lower confidence is eliminated. The threshold value τ is set in some embodiments to 0.5.

This is not done for all findings, but only for those that cannot share the same area (e.g., fillings and crowns);

Subphase of 2234*d* mask contour finding, where the threshold value for conversion to binary masks in some embodiments is 0.4;

Subphase of approximation of contour mask 2235*d;*

Subphase of subdivision 2236*d;*

Figure 11:
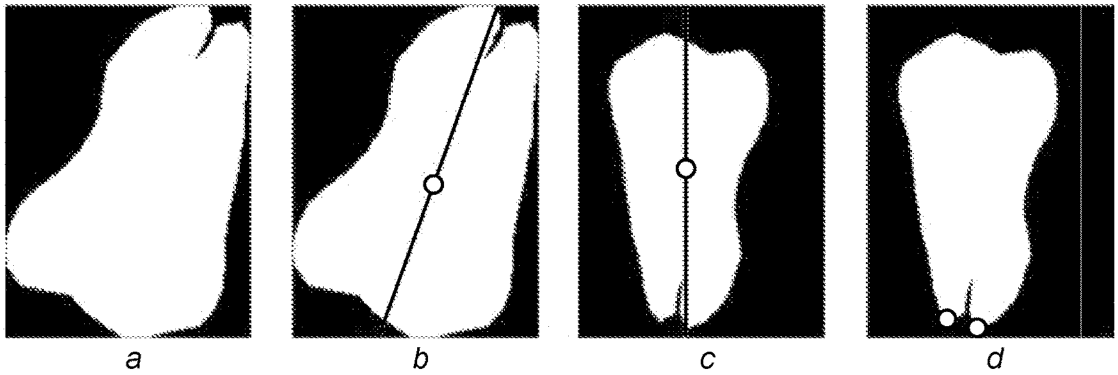
FIG. 11 shows the operations of how the root apexes of a tooth are found during the post-processing phase "Checking root canal treatments" of the tooth-level findings inference module in the inference operation mode.

Subphase of removal of elements on the outside of tooth 2237*d* tooth, in which for an existing tooth outline, if a detection is outside the area bordered by the outline, then it is removed. This subphase takes as input the tooth templates detected by the tooth detection inference module;

Subphase 2238*d* checking for too short root canal treatment, in which the aim of this operation is to flag the presence of root canal treatments that are too short. With reference to FIG. 11, the phases used are listed:

a. Where there is the binary mask of a tooth, Principal Component Analysis (PCA) is applied, and the center of the tooth and its orientation are extracted. The orientation vector corresponds to the first eigenvector obtained from PCA (the first of the principal components);

b. the mask of the tooth and that of the detected root canal treatment are appropriately rotated so that the roots are always at the bottom;

c. for the mask of the root canal treatment, we take those points whose coordinate y is a local minimum value with respect to the vertical axis (with some tolerance), for the tooth mask, on the other hand, only those points corresponding to the local minimum values that are lower than the center are taken. The minimum points of the tooth correspond to the root apices;

d. for each minimum point of root canal treatment and root apex of the tooth, the Euclidean distance is calculated. If a minimum point of the root canal cure does not have at least one Euclidean distance less than a threshold, t then that root canal cure is reported as too short. The threshold value used is $\tau=\theta\cdot$Length of Tooth where $\theta\in[0, 1]$ is a configurable parameter.

The subphase of checking missing internal screws 2239*d*, in which the case where it is checked whether an implant lacks an internal screw.

The output of this model inference module findings on single tooth 22*d* is a list of findings (each consisting of label, confidence, bounding box and template) and a list of alerts regarding the detection of short root canal cures.

Figure 14:
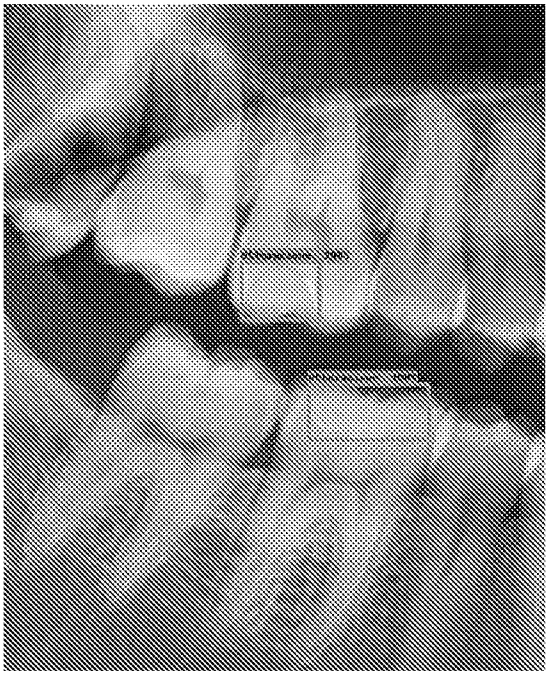
FIG. 14 shows the results of the combined outcome of the mouth-level detection and tooth-level findings models in inference operation mode.

A visual example of the findings obtained by combining the output of the inference module of mouth-level findings and that of single-tooth findings is shown in FIG. 14.

Figure 15:
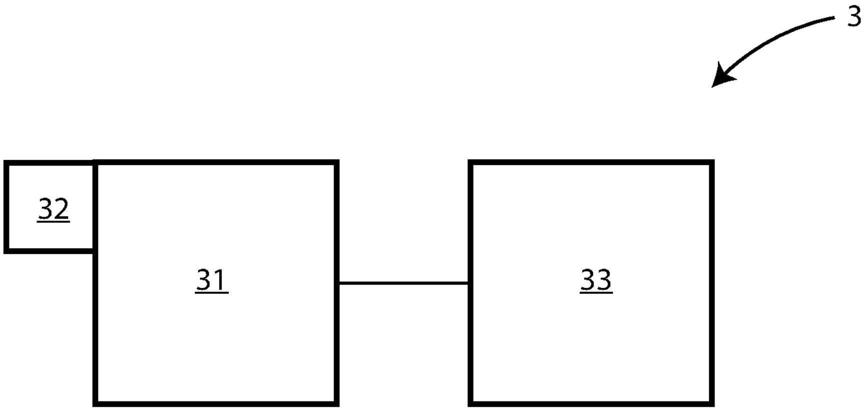
FIG. 15 shows a system for analysing X-Rays according to the present invention.

Referring now to FIG. 15, a possible embodiment of a system for the analysis of X-Rays 3 is shown, which basically comprises a logical processing unit 31 having an input port 32 for the acquisition of X-Rays, typically by means of digitized signals, connected to an interface unit 33, such as a display and related means of interaction, such as a keyboard, mouse and the like, for the detection of processing results. Processing Logic Unit 31 is configured to perform the X-Ray analysis method described above.

Benefits

One advantage of the present invention is to provide an aid for medical radiologists, and dentists in particular, to detect and locate teeth.

An additional advantage of the present invention is to enable the dentist to make correct diagnoses and therapies, enabling accurate treatments.

It is also an advantage of the present invention to enable automatic analysis of X-Ray images, in other words, the obtaining of data for in-depth epidemiological studies and analysis of the success of dental care.

Experimental Results

To assess the quality of the proposed solution, after filtering the notes (subphase 131), the X-Ray images and notes were divided into two datasets: One for learning and the other for testing. Twenty percent of the available data was reserved for testing.

The following table shows the experimental results for the teeth model inference module 22*b* and the anatomical model inference module 22*a*.

The measures used for evaluation are COCO mean average precision (mAP) and COCO mean average recall (mAR). The closer these measures are to 100, the higher the goodness of the detection system.

These two metrics were applied for both bounding boxes (finding) and masks (Segmentation). Specifically, for the tooth model inference module 22*b* a confidence threshold of 0.2 was set and as a threshold value for conversion to binary masks 0.4; while for the anatomical model inference module 22*a* a confidence threshold of 0.5 was set and as a threshold value for conversion to binary masks 0.4. The threshold values were determined by choosing those with which the best results were obtained.

For the teeth 22*b* model inference module, the full module (Teeth BLP) and a version without the BLP model were tested using the classical non-maximum suppression algorithm (Teeth NMS) instead. The results show that using the BLP model improves system performance in terms of detection quality.

| Inference | # Test | Finding | | Segmentation | |
|---|---|---|---|---|---|
| Module | Images | mAP | mAR | mAP | mAR |
| NMS Teeth | 88 | 70.0 | 72.9 | 68.9 | 71.5 |
| BLP Teeth | 88 | 70.8 | 73.8 | 69.7 | 72.5 |
| Anatomical | 95 | 64.4 | 71.0 | 45.9 | 52.4 |

REFERENCES

Chen, Y.-w., Stanley, K., & Att, W. (2020). Artificial intelligence in dentistry: Current applications and future perspectives. Quintessence International, 51 (3), 248-257.

Girshick, R. (2015). Fast R-CNN. IEEE International Conference on Computer Vision (ICCV) (p. 1440-1448). Santiago, Chile: IEEE.

He, K., & Georgia Gkioxari, P. D. (2017). Mask R-CNN. 2017 IEEE International Conference on Computer Vision (ICCV) (p. 2980-2988). Venice, Italy: IEEE. Taken from https://arxiv.org/abs/1703.06870

Loshchilov, I., & Hutter, F. (2017). SGDR: Stochastic Gradient Descent with Warm Restarts. 5th International Conference on Learning Representations. Taken from https://openreview.net/pdf?id=Skq89Scxx Ren, S., He, K., Girshick, R., & Sun, J. (2015). Faster R-CNN: Towards Real-Time Object detection with Region Proposal Networks. Advances in Neural Information Processing Systems, 28. Taken from https://arxiv.org/abs/1506.01497

Suzuki, S., & Abe, K. (1985). Topological structural analysis of digitized binary images by border following. Computer Vision, Graphics, and Image Processing, 30 (1), 32-46.

The present invention has been described by way of illustration, but not limitation, in accordance with its preferred forms of embodiment, but it is to be understood that variations and/or modifications may be made by those skilled in the art without departing from the relevant scope of protection as defined by the appended claims.

The invention claimed is:

1. A computer-implemented method of analyzing X-Ray pictures, comprising an operational inference step, the operational inference step comprising:

detecting (21) an X-Ray image; and performing at least one inference form (22*a*, 22*b*, 22*c*, 22*d*) to obtain detection and distinction of teeth, detection and distinction of anatomical parts of a mouth, and/or detection and distinction of pathological and non-pathological findings;

wherein performing at least one inference form (22*a*, 22*b*, 22*c*, 22*d*) includes the following sub-steps:

performing an anatomical model inference module (22*a*);

performing a tooth model inference module (22*b*);

performing an inference module for a model of findings in the mouth (22*c*); and performing an inference form of a model findings on a single tooth (22*d*);

wherein said tooth model inference module (22*b*) includes a post-processing step (223*b*), comprising the sub-steps of:

class-dependent non-maximum suppression or suppression of class-dependent non-maximums (2231*b*), in which, where there are two bounding boxes belonging to a same class such that said two bounding boxes identify a same tooth, if said two bounding boxes overlap with an intersection value greater than or equal to a predefined threshold, a box of said two bounding boxes with lower confidence is eliminated;

application of a BLP model (2232*b*), in which constraints are placed on tooth ordering;

mask contour detection (2233*b*), in which masks obtained from a model are converted to point coordinates as polygons representing an outline of a detected feature;

mask contour approximation (2234*b*); and subdivision (2235*b*), in which the polygons obtained in said mask contour approximation (2234*b*) are refined.

2. The computer-implemented method according to claim 1, wherein said inference module for findings on a single tooth model (22*d*) is performed following said tooth model inference module (22*b*), and wherein said anatomical model inference module (22*a*), said tooth model inference module (22*b*) and said mouth findings model inference module (22*c*) are run in parallel.

3. The computer-implemented method according to claim 1, wherein said anatomical model inference module (22*a*) and said inference module for findings on a single tooth model (22*d*) acquire, as input, geometric coordinates that make up tooth outlines detected by said tooth model inference module (22*b*).

4. The computer-implemented method according to claim 1, wherein said anatomical model inference module (22*a*), said tooth model inference module (22*b*), said mouth findings model inference module (22*c*) and said single tooth findings model inference module (22*d*) comprises a pre-processing step (221*a*, 221*b*, 221*c*, 221*d*), comprising the sub-steps of:

Contrast Limited Adaptive Histogram Equalization (CLAHE) (2211*a*, 2211*b*, 2211*c*, 2211*d*), so as to change the X-ray image in contrast; and resizing (2212*a*, 2212*b*, 2212*c*, 2212*d*) of the X-ray image.

5. The computer-implemented method according to claim 1, wherein said model inference module findings on a single tooth (22*d*) includes a pre-processing step (221*d*), in which, after the sub-step of CLAHE (2211*d*), there is an additional sub-step of single tooth clipping (2213*d*), which, for each tooth present in the X-Ray image, clips an area of an original image containing the tooth.

6. The computer-implemented method according to claim 1, wherein said anatomical model inference module (22*a*) includes a post-processing step (223*a*), comprising the sub-steps of:

non-maximum suppression or suppression of non-maximums (2231*a*), in which, where there are two bounding boxes, if those two bounding boxes overlap with an intersection value greater than or equal to a predefined threshold, the bounding box with lower confidence is eliminated;

mask contour detection (2232*a*), in which masks obtained from a model are converted to point coordinates as polygons representing an outline of a detected feature;

mask contour approximation (2233*a*);

subdivision (2234*a*), in which the polygons obtained in said mask contour approximation sub-step (2233*a*) are refined; and root invasion detection (2235*a*), which comprises detecting whether there are parts of a tooth invading maxillary sinuses or mandibular canals hosting lower alveolar nerves.

7. The computer-implemented method according to claim 1, wherein said inference module for the model of findings in the mouth (22*c*) includes a post-processing step (223*c*), comprising the sub-steps of:

class-dependent non-maximum suppression or suppression of class-dependent non-maximums (2231*c*), in which, where there are two bounding boxes belonging to a same class such that said two bounding boxes identify a same finding, if said two bounding boxes overlap with an intersection value greater than or equal to a predefined threshold, the bounding box with lower confidence is eliminated;

non-maximum suppression or suppression of non-maximums (2232*c*), in which, where there are two bounding boxes, if the two bounding boxes overlap with an intersection value greater than or equal to a predefined threshold, the bounding box with lower confidence is eliminated;

mask contour detection (2233*c*), in which masks obtained from the model are converted to point coordinates as polygons representing an outline of a detected feature;

mask contour approximation (2234*c*); and subdivision (2235*c*), in which the polygons obtained in said mask contour approximation sub-step (2233*a*) are refined.

8. The computer-implemented method according to claim 7, wherein said post-processing step (223*d*) of the inference module of single-tooth model findings (22*d*) includes the sub-steps of:

sub-step of class-dependent non-maximum suppression or suppression of class-dependent non-maximums (2231

*d*), in which, where there are two bounding boxes belonging to a same class such that said two bounding boxes identify a same finding, if said two bounding boxes overlap with an intersection value greater than or equal to a predefined threshold, the bounding box with lower confidence is eliminated;

sub-step of non-maximum suppression or suppression of non-maximums (2232*d*) for some classes of findings in which, where there are two bounding boxes of features belonging to classes that cannot share a same area, if said two bounding boxes overlap with an intersection value greater than or equal to a predefined threshold, the bounding box with lower confidence is eliminated;

sub-step of mask non-maximum suppression or suppression of non-maximum masks (2233*d*) based on intersection over minimum area, which is class-independent, for some classes of findings, to eliminate findings that are also partially contained in other findings and cannot share a same area;

mask contour detection sub-step (2234*d*), in which masks obtained from a model are converted into point coordinates as polygons representing an outline of a detected feature;

mask contour approximation sub-step (2235*d*);

subdivision sub-step (2236*d*), in which the polygons obtained in said mask contour approximation sub-step (2234*b*) are refined;

out-of-area tooth element removal sub-step (2237*d*), in which where there is a tooth outline, if a detection is outside an area bordered by the tooth outline, then the tooth element is removed;

short root canal treatment check sub-step (2238*d*), to signal a presence of root canal treatments that are too short; and missing internal screw check subphase (2239*d*), in which it is checked whether an implant lacks an internal screw.

9. The computer-implemented method according to claim 1, further comprising an operational learning step (1), comprising the following steps:

acquiring X-Ray images (11);

acquiring notes (12) associated with said X-Ray images (11); and performing at least one learning procedure (13*a*, 13*b*, 13*c*, 13*d*), for element finding.

10. The computer-implemented method according to claim 9, wherein the step of performing at least one learning procedure (13*a*, 13*b*, 13*c*, 13*d*) includes one or more of the following sub-steps:

performing an anatomical learning procedure (13*a*) for the detection of anatomical parts;

performing a tooth learning procedure (13*b*) for tooth finding;

performing a mouth findings learning procedure (13*c*) for mouth-level findings; and performing a tooth detection learning procedure (13*d*) for tooth-level findings.

11. The computer-implemented method according to claim 10, wherein a plurality of learning procedures (13*a*, 13*b*, 13*c*, 13*d*) are performed in parallel.

12. The computer-implemented method according to claim 11, wherein each of said plurality of learning procedures generate one or more models that have as output for each detected element:

a confidence vector;

a label, representing a highest confidence class of the detected element;

a bounding box of an object area; and a matrix of values, preferably real e [0, 1], where a value of each component $m_{ij}$ represents a confidence that a pixel on a row I, column j belongs to a detected class.

13. The computer-implemented method according to claim 10, wherein performing at least one learning procedure (13*a*, 13*b*, 13*c*, 13*d*) includes the following sub-steps:

filtering incomplete notes (131);

flipping randomly with respect to a horizontal axis (1332);

rotating randomly (1333);

adjusting random contrast (1334), in which a contrast of images is adjusted by a random factor within a range;

adjusting random brightness (1335), in which a brightness of images is adjusted by a random factor within a range; and resizing said images (134).

14. The computer-implemented method according to claim 13, wherein said teeth model learning procedure (13*b*), includes the following sub-step:

performing a synthetic endoral generation (1331), to obtain periapical and bitewing-like X-Ray images from orthopanoramics.

15. The computer-implemented method according to claim 14, characterized by the fact that said notes (12) include, for each element, a label suitable for identifying a class to which a reference element belongs, a series of points defining a polygonal outline of said reference element, and a bounding box within which the reference element is contained.

16. The computer-implemented method according to claim 9, wherein said operational learning step and said operational inference step are alternated in time.

17. A system (3) for analyzing X-Ray pictures, comprising:

a logical processing unit (31) having an input port (32) for acquiring X-Rays, and an interface unit (33), for detecting and displaying processing results, wherein said logical processing unit (31) performs the computer-implemented method of analyzing X-Ray pictures according to claim 1.

* * * * *